United States Patent [19]

van der Stoel

[11] Patent Number: 4,639,525

[45] Date of Patent: Jan. 27, 1987

[54] PROCESS FOR THE PREPARATION OF PYRIDONE-2 BY DEMETHYLATION

[75] Inventor: Roland E. van der Stoel, Born, Netherlands

[73] Assignee: Stamicarbon B.V., Geleen, Netherlands

[21] Appl. No.: 671,308

[22] Filed: Nov. 14, 1984

[30] Foreign Application Priority Data

Nov. 28, 1983 [NL] Netherlands ............... 8304065

[51] Int. Cl.$^4$ ............................................. C07D 213/64
[52] U.S. Cl. ........................................ 546/290; 546/250
[58] Field of Search ................................ 546/290, 250

[56] References Cited

PUBLICATIONS

Abramovitch, Pyridine and its Derivatives, Supplement Part Three, pp. 795–796, Wiley–Interscience Pub., vol. 14 (1974).

Van Der Stoel, Chem. Abstracts, vol. 103, (No. 23), Abst. No. 196,010r, Dec. 9, 1985.

Chem. Abstracts vol. 89, No. 15, p. 580, Abs. No. 129404b (Oct. 9, 1978).

*Primary Examiner*—Alan L. Rotman
*Attorney, Agent, or Firm*—Cushman, Darby & Cushman

[57] ABSTRACT

Process for the preparation of 2-pyridone in the gas phase comprising contacting 6-methyl-2-pyridone with a metallic dealkylation catalyst in the presence of water at a temperature of 200°–500° C.

5 Claims, No Drawings

PROCESS FOR THE PREPARATION OF PYRIDONE-2 BY DEMETHYLATION

BACKGROUND OF THE INVENTION

The invention relates to a process for the preparation of 2-pyridone.

According to prior art, 2-pyridone can be prepared in the liquid phase in a three-stage process starting from pyridine. In the first stage, pyridine is converted with hydrogen peroxide practically quantitatively to pyridine-1-oxide. The reaction medium is acetic acid. The first stage is described in R. A. Abramovitch and E. M. Smith, pyridine and its derivatives, Volume 14, Supplement Part 2, Chapter 4 at page 5. In the second stage, the stage one product is converted with acetic anhydride into acetoxypyridine where in the second stage the yield is not more than 65% (see *Chemical Abstracts* 63: 14807 f). The final stage, a hydrolysis stage, proceeds quantitatively. See also *Chemical Abstracts* 63: 14807 f. The above-described process is objectionable because it is a laborious liquid-phase process and also because the starting material, pyridine, is very costly. In the second stage, conversion with acetic anhydride into acetoxypyridine, the yield is not more than 65% (see *Chemical Abstracts* 63: 14807 f). A hydrolysis stage as final stage proceeds quantitatively (vide also *Chemical Abstracts* 63: 14807 f). Such a process is objectionable because of the laboriousness of a liquid-phase process as well as the costly starting material i.e. pyridine.

According to another known process (see Japanese Patent Application No. 51143672) 2,4-hexadienamide can be converted to 2-pyridone in the presence of a palladium salt and a tertiary amine in an aprotic solvent through ring closure, with a yield of 75%. The objectionability of a liquid-phase process exists here, too. Also, the starting material, a poly-unsaturated carboxamide, is costly.

Alternatively, as described in J. Heterocyclic. Chem. 16 (1979) pages 1283 through 1286, pyridine can be oxidized in the gas phase to 2-pyridone in the presence of $CuSO_4.5H_2O$ at 300° C. The selectivity of this conversion is 95% but the conversion is only 20%. This process is objectionable because high pressure equipment is required in order to conduct the conversion. In addition, this process suffers from the further defect in that it also uses the costly starting material, pyridine.

DESCRIPTION OF THE INVENTION

The present invention provides a process for the preparation of 2-pyridone which is very attractive from an economy point of view. The process according to the invention for the preparation of 2-pyridone in the gas phase is characterized in that 6-methyl-2-pyridone is contacted with a metallic catalyst in the presence of water at a temperature of 200° to 500° C. and 2-pyridone is recovered from the reaction mixture so produced.

In the process according to the invention it is possible to achieve a selectivity in excess of 80% at a very reasonable conversion of 6-methyl-2-pyridone, while the catalyst remains active for prolonged periodes of time and can be regenerated readily.

The process according to the invention starts from 6-methyl-2-pyridone, which according to the non-prepublished Netherlands Patent Application No. 8301416 can be produced in a suitable and economically attractive manner by reacting an oxoalkanecarboxylic acid, or an ester thereof, with a primary amine. Alternatively, one could use a di, tri and/or tetraalkyl-2-pyridone as starting compound.

Advantageously, the process of the present invention can be carried out at atmospheric pressure but lower or higher pressures may be applied also.

The temperature at which 6-methyl-2-pyridone is contacted with the catalyst is preferably 250° C. to 350° C.

Examples of metallic dealkylation catalysts that may be applied in the process according to the invention are nickel, cobalt, platinum, palladium and ruthenium. Nickel is preferably used as catalyst. The above-mentioned metals may be attached to a suitable carrier.

In the process according to the present invention the amount of water may be varied between, for instance, 1 and 60 moles per mole of starting compound but it is preferably 5 to 40 moles per mole of starting compound.

For the practical realization of the process according to the invention use may be made of the commonly known embodiments of gas-phase reactions such as those in which the gaseous starting mixture is passed over the catalyst in the form of a fixed bed or a fluid bed. The space velocity may be varied between, for instance, 0.001 and 2 g of starting compound per milliliter of catalyst material (packed volume) per hour.

When catalyst activity becomes too low the catalyst material may be regenerated in a straightforward manner, for instance, by treating the catalyst material with hydrogen and/or steam at a temperature at least equal to the reaction temperature applied.

The process according to the invention may produce—besides 2-pyridone—minor amounts of pyridine and alpha-picoline. By cooling the gas mixture obtained, which contains also unconverted 6-methyl-2-pyridone, it is possible to produce a condensate from which the desired 2-pyridone may be recovered by, for instance, crystallization or distillation.

The compounds obtained in the process according to the invention may be applied in, for instance, the preparation of crop protection agents and anti-inflammatory drugs.

The following examples will further illustrate this invention.

EXAMPLES I-IV

A gaseous mixture of 6-methyl-2-pyridone and water is passed at atmospheric pressure down a vertical tubular reactor 17 mm in diameter and 400 mm long provided with a heating jacket and incorporating a zone of 10 ml of catalyst. The catalyst zone is bordered at the underside by a zone of 5 ml and at the top side by a zone of 75 ml of inert ceramic material. Nickel is used as a catalyst, which is commercially available under the name of Harshaw Ni 1404. This catalyst contains 62 vol.% nickel relative to the total amount of catalyst. The bulk density of the catalyst is 1.43 g/ml.

After several operating periods the gaseous reaction mixture obtained is condensed and the liquid so obtained is analysed through gas chromatography and liquid chromatography. The conversion and yield of 2-pyridone, pyridine and alpha-picoline is calculated from the analysis of the liquid, the amount of liquid and the corresponding amount of 6-methyl pyridone-2 that has passed through the reactor. The results are provided in the table.

EXAMPLE V 6-methyl-2-pyridone is converted in the manner described in Examples I–IV except that use is made of a nickel catalyst which is commercially available under the name of Girdler G78. This catalyst contains 57 wt.% nickel relative to the total amount of catalyst with a bulk density of 0.89 g/ml. Before the reaction is commenced the catalyst is activated with hydrogen for 16 hours at 310° C. The results are provided in the table.

EXAMPLE VI 6-methyl-2-pyridone is converted in the manner described in Examples I–IV. Use is made of a cobalt catalyst which has been activated with hydrogen for 16 hours at 310° C. This catalyst is commercially available under the name of Harshaw Co 1606 and contains 85 wt.% cobalt relative to the total amount of catalyst. The bulk density of the catalyst is 2.32 g/ml. The results are provided in the table.

TABLE

| | Example | | | | | |
|---|---|---|---|---|---|---|
| | I | II | III | IV | V | VI |
| Operating period in hours | 42 | 44 | 27 | 15 | 27 | 25 |
| Temperature of the catalyst zone in °C. | 300 | 300 | 310 | 310 | 310 | 310 |
| Moles of water per mole of 6-methyl-2-pyridone | 20 | 20 | 20 | 30 | 20 | 20 |
| Space velocity in g of 6-methyl-2-pyridone per hour per ml of catalyst | 0.12 | 0.22 | 0.20 | 0.20 | 0.20 | 0.20 |
| Conversion % | 54 | 29 | 32 | 31 | 24 | 42 |
| Selectivity for 2-pyridone % | 55 | 86 | 69 | 80 | 84 | 26 |
| Selectivity for pyridine % | 8 | 3 | 8 | — | — | 14 |
| Selectivity for alpha-picoline % | 2 | 2 | 2 | — | — | 10 |

I claim:
1. A gas phase process for preparing 2-pyridone, that 6-methyl-2-pyridone is contacted with a metal catalyst selected from the group consisting of nickel, cobalt, platinum, palladium and ruthenium, in the presence of water at a temperature of 200° C. to 500° C. to obtain a reaction mixture containing 2-pyridone; and
subsequently recovering 2-pyridone from the reaction mixture so produced.
2. The process according to claim 1 wherein said metallic catalyst is nickel.
3. The process according to claim 1 where in the 6-methyl-2-pyridone is contacted with said metallic catalyst at a temperature of 250° C. to 350° C.
4. The process according to claim 1 wherein 5 to 40 moles of water are applied per mole of 6-methyl-2-pyridone.
5. A gas phase process for preparing 2-pyridone comprising:
contacting 6-methyl-2-pyridone with a metallic catalyst selected from the group consisting of nickel, cobalt, platinum, palladium and ruthenium;
in the presence of 5 to 40 moles of water per mole of 6-methyl-2-pyridone at a temperature of about 250° C. to 350° C. whereby a reaction mixture is obtained which contains 2-pyridone; and
subsequently recovering 2-pyridone from the thus obtained reaction mixture.

* * * * *